(12) United States Patent
An et al.

(10) Patent No.: US 11,186,866 B2
(45) Date of Patent: Nov. 30, 2021

(54) METHOD FOR MULTIPLEX DETECTION OF METHYLATED DNA

(71) Applicant: GENOMICTREE, INC., Daejeon (KR)

(72) Inventors: Sungwhan An, Daejeon (KR); TaeJeong Oh, Daejeon (KR)

(73) Assignee: GENOMICTREE, INC., Daejeon (KR)

(*) Notice: Subject to any disclaimer, the term of this patent is extended or adjusted under 35 U.S.C. 154(b) by 281 days.

(21) Appl. No.: 16/339,694

(22) PCT Filed: Sep. 29, 2017

(86) PCT No.: PCT/KR2017/010907
§ 371 (c)(1),
(2) Date: Apr. 4, 2019

(87) PCT Pub. No.: WO2018/066910
PCT Pub. Date: Apr. 12, 2018

(65) Prior Publication Data
US 2019/0284608 A1    Sep. 19, 2019

(30) Foreign Application Priority Data

Oct. 6, 2016  (KR) .................. 10-2016-0129110

(51) Int. Cl.
*C12Q 1/686* (2018.01)
*C12Q 1/6806* (2018.01)
*C12Q 1/68* (2018.01)

(52) U.S. Cl.
CPC .............. *C12Q 1/686* (2013.01); *C12Q 1/68* (2013.01); *C12Q 1/6806* (2013.01); *C12Q 2600/154* (2013.01); *C12Q 2600/16* (2013.01)

(58) Field of Classification Search
CPC .................. C12Q 1/686; C12Q 2600/154
See application file for complete search history.

(56) References Cited

U.S. PATENT DOCUMENTS

| 5,784,146 A | 7/1998 | Nanjo et al. |
| 7,364,855 B2 | 4/2008 | Andersen et al. |

(Continued)

FOREIGN PATENT DOCUMENTS

| KR | 1020120067673 A | 6/2012 |
| KR | 10201501 14844 A | 10/2015 |

OTHER PUBLICATIONS

Cheng et al., Multiplexed profiling of candidate genes for CpG island methylation status using a flexible PCR/LDR/Universal Array assay, Genome Res., vol. 16, gr.4181406, pp. 1-8 (Year: 2006).*

(Continued)

*Primary Examiner* — Teresa E Strzelecka
(74) *Attorney, Agent, or Firm* — Hultquist, PLLC; Steven J. Hultquist

(57) ABSTRACT

The present disclosure relates to a method of detecting methylation of target DNA in a multiplex manner and a composition for detecting methylation of target DNA, and more particularly to a method for detecting methylation of target DNA, comprising: constructing an oligonucleotide, which comprises a target-specific sequence capable of binding complementarily to the target DNA and a universal primer that does not bind complementarily to the target DNA; linearly amplifying the target DNA for linear target enrichment by using the oligonucleotide as a primer; and amplifying the linearly amplified target DNA using an oligonucleotide, which is capable of binding complementarily to the linearly amplified target DNA, a universal primer, and a probe.

22 Claims, 3 Drawing Sheets

Specification includes a Sequence Listing.

(56) References Cited

U.S. PATENT DOCUMENTS

2010/0028890 A1 2/2010 Boyd
2010/0144867 A1 6/2010 Barany et al.
2012/0252013 A1 10/2012 Guo

OTHER PUBLICATIONS

Kristensen, E., et al., "Organic carbon dynamics in mangrove ecosystems: A review", "Aquatic botany", 2008, pp. 201-219, vol. 89, Publisher: Elsevier.

Moskalev, E., et al., "Correction of PCR-bias in quantitative DNA methylation studies by means of cubic polynomial regression", "Nucleic Acids Research", 2011, p. e77, vol. 39, No. 11, Publisher: Oxford University Press.

Kang, Y., et al., "Quantitative and multiplexed DNA methylation analysis using long-read single-molecule real-time bisulfite sequencing (SMRT-BS)", "BMC Genomics", 2015, pp. 1-10, vol. 16, No. 350, Publisher: BioMed Central.

Oh, T., et al., "Genome-Wide Identification and Validation of a Novel Methylation Biomarker, SDC2, for Blood-Based Detection of Colorectal Cancer", "The Journal of Molecular Diagnostics", Jul. 2013, pp. 498-507, vol. 15, No. 4.

Kang, Y., et al., "Quantitative and Multiplexed DNA Methylation Analysis Using Long-Read Single-Molecule Real-Time Bisulfite Sequencing (SMRT-BS)", "BMC Genomics", 2015, pp. 1-10, vol. 16, No. 350.

Oh, T.J., et al., "Feasibility of quantifying SDC2 methylation in stool DNA for early detection of colorectal cancer", "Clinical Epigenetics", 2017, pp. DOI 10.1186/s13148-017-0426-3, vol. 9, No. 126, Publisher: BioMed Central.

Pfeifer, G.P., et al., "Analysis of Methylation and Chromatin Structure", "Methods of Enzymology", 1993, pp. 567-583, vol. 225, Publisher: Academic Press, Inc.

* cited by examiner

[Fig. 1]
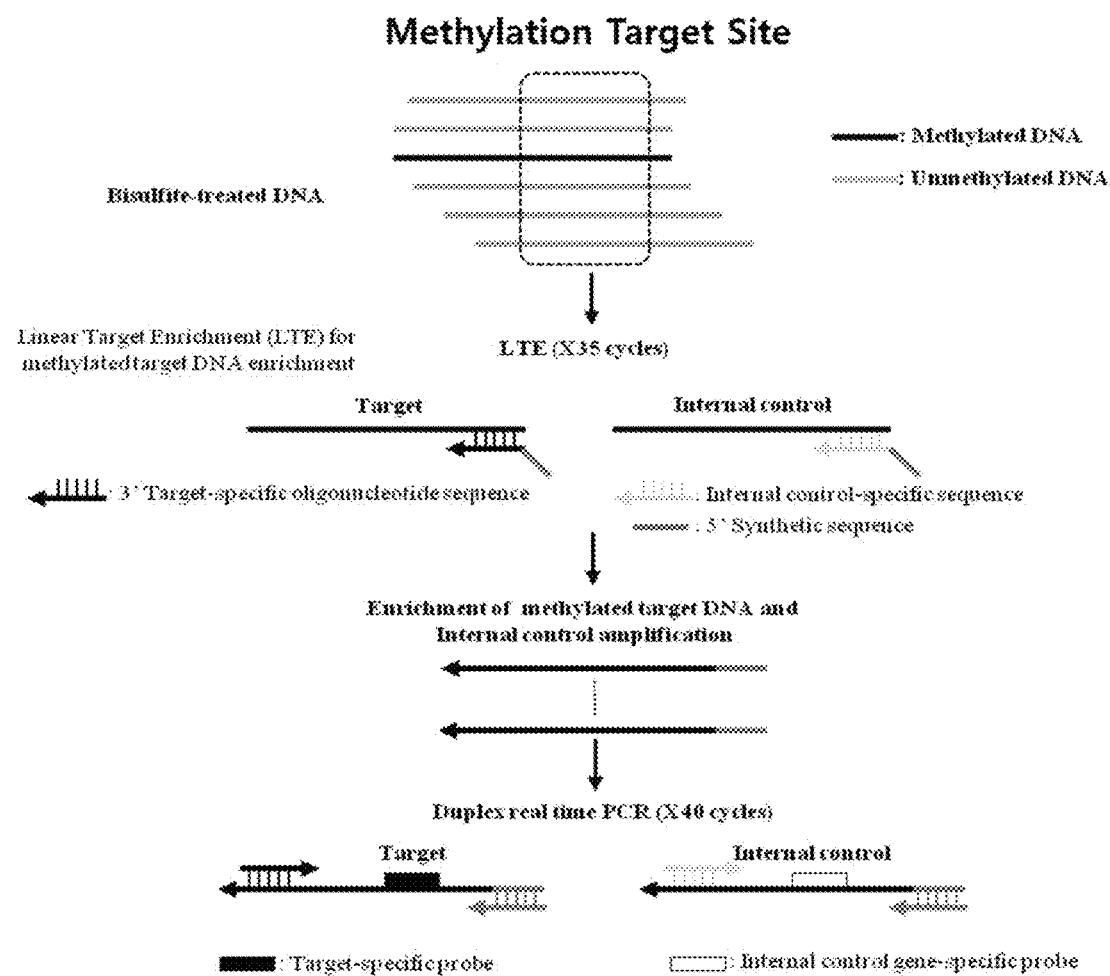

[Fig. 2]
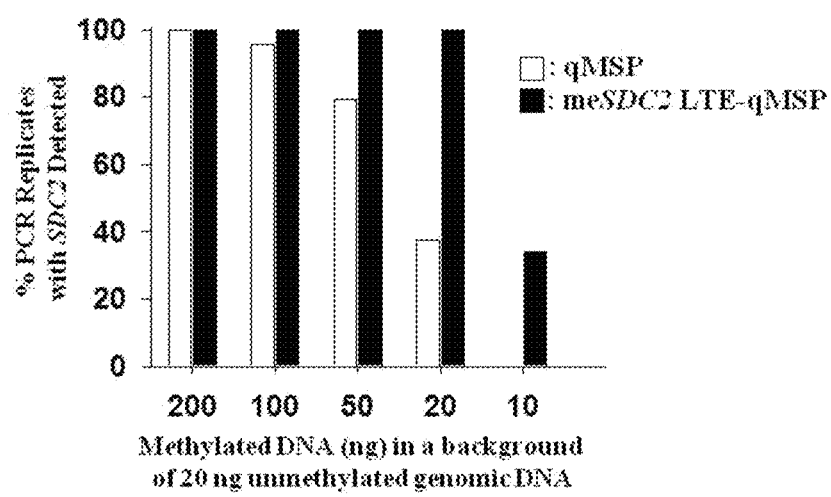
[Fig. 3]
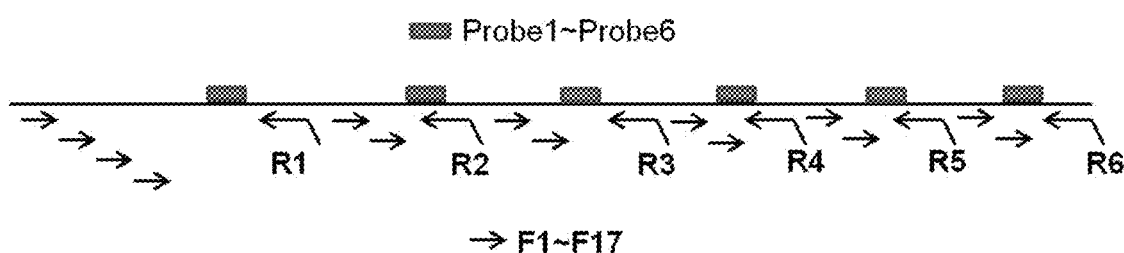

【Fig. 4a】
A
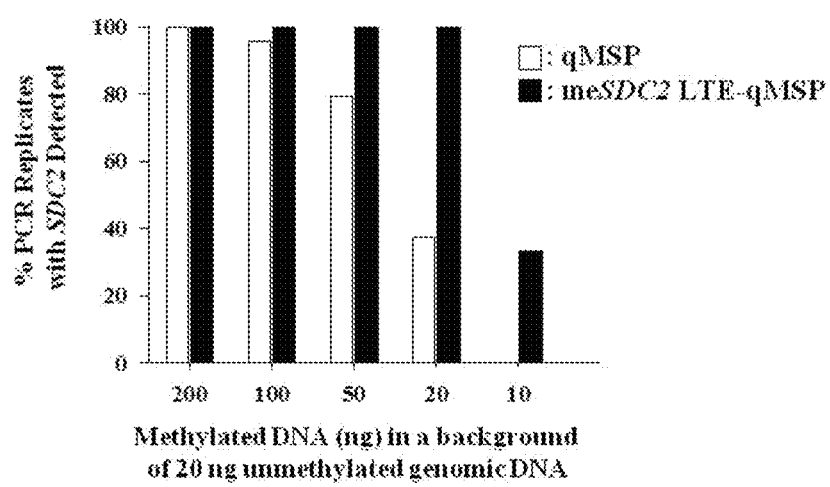
【Fig. 4b】
B
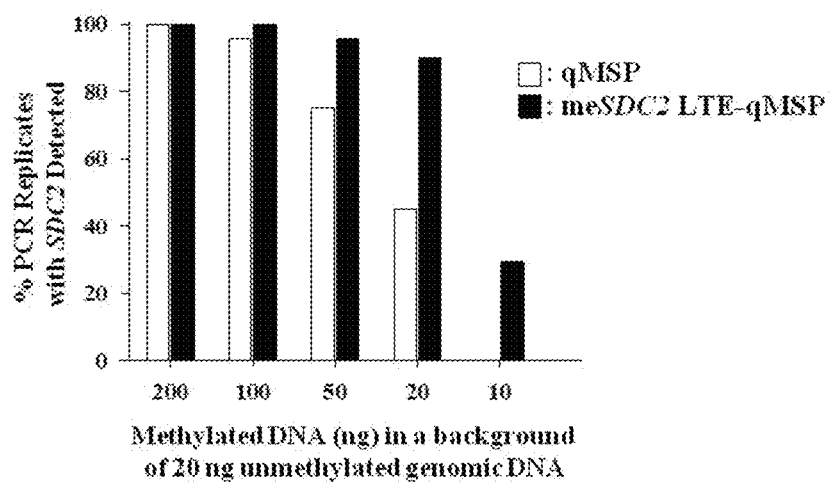

11,186,866 B2

METHOD FOR MULTIPLEX DETECTION OF METHYLATED DNA

CROSS-REFERENCE TO RELATED APPLICATIONS

This application is a U.S. national phase under the provisions of 35 U.S.C. § 371 of International Patent Application No. PCT/KR17/10907 filed Sep. 29, 2017, which in turn claims priority of Korean Patent Application No. 10-2016-0129110 filed Oct. 6, 2016. The disclosures of International Patent Application No. PCT/KR17/10907 and Korean Patent Application No. 10-2016-0129110 are hereby incorporated herein by reference in their respective entireties, for all purposes.

TECHNICAL FIELD

The present disclosure relates to a method of detecting methylation of target DNA in a multiplex manner and a composition for detecting methylation of target DNA, and more particularly to a method for detecting methylation of target DNA, comprising: constructing an oligonucleotide, which comprises a target-specific sequence capable of binding complementarily to the target DNA and an artificial primer not complementary to the target DNA; linearly amplifying the target DNA for linear target enrichment (hereinafter referred to as LTE) by using the oligonucleotide as a primary primer; amplifying the linearly amplified target DNA using an oligonucleotide separate from the oligonucleotide used as a primary primer, which is capable of binding complementarily to the linearly amplified target DNA, and a universal primer not complementary to the linearly amplified target DNA; and detecting the presence or absence of the amplification product by a probe.

BACKGROUND ART

In the genomic DNA of mammalian cells, there is the fifth base in addition to A, C, G and T, namely, 5-methylcytosine, in which a methyl group is attached to the fifth carbon of the cytosine ring (5-mC). 5-mC is always attached only to the C of a CG dinucleotide (5'-mCG-3'), which is frequently marked CpG. The C of CpG is mostly methylated by attachment with a methyl group. The methylation of this CpG inhibits a repetitive sequence in genomes, such as Alu or transposon, from being expressed. In addition, this CpG is a site where an epigenetic change in mammalian cells appears most often. The 5-mC of this CpG is naturally deaminated to T, and thus, the CpG in mammal genomes shows only 1% of frequency, which is much lower than a normal frequency ($\frac{1}{4} \times \frac{1}{4} = 6.25\%$).

Regions in which CpGs are exceptionally integrated are known as CpG islands. The term "CpG islands" refer to sites which are 0.2-3 kb in length, and have a C+G content of more than 50% and a CpG ratio of more than 3.75%. There are about 45,000 CpG islands in the human genome, and they are mostly found in promoter regions regulating the expression of genes. Actually, the CpG islands occur in the promoters of housekeeping genes accounting for about 50% of human genes. It is known that aberrant DNA methylation occurs mainly in the 5' regulatory region of the gene to reduce the expression of the gene.

Herein, the 5' regulatory region of the gene includes a promoter region, an enhancer region and a 5' untranslated region. Recently, an attempt to examine the promoter methylation of tumor-related genes in blood, sputum, saliva, feces or urine and to use the examined results for the diagnosis and treatment of various cancers, has been actively conducted.

It is well known that DNAs are released from abnormal cells in the cancer tissue of cancer patients into blood by processes including apoptosis and necrosis, and thus exist as cell-free tumor DNA in the serum or plasma of the blood, and methylated DNA fragments are also present in the cell-free tumor DNA. The presence of this aberrant DNA methylation has been used as a marker for diagnosing cancer.

Meanwhile, generally, methods for analyzing gene methylation are performed by detecting a control gene, which is not involved in methylation, by PCR in order to confirm the suitability of the PCR and the presence or absence of input DNA, and performing PCR for detecting methylation of target DNA in parallel thereto.

In particular, as methods of analyzing methylation by real-time PCR, the following methods can be taken into consideration: i) a method that uses primers independent of methylation of target DNA as primers for real-time PCR and uses a methylation-specific detection primer, which is capable of hybridizing to the methylated target DNA, for detection of the PCR amplification product; ii) a method that uses target DNA methylation-specific primers as primers for real-time PCR and uses a detection probe capable of hybridizing to a methylation-independent sequence contained in the PCR amplification product; and iii) a method that uses target DNA methylation-specific primers as primers for real-time PCR and uses a methylation-specific detection probe, which is capable of hybridizing to methylated target DNA, for detection of the PCR amplification product.

However, these methods all use non-enriched DNA directly as a template and necessarily use two primers (forward and reverse) for amplifying target DNA, at the same time. Accordingly, there is a problem that two primers are further required at a time whenever the target to be amplified in one tube (single reactor) increases.

Primers for multiplex PCR are designed such that different primers in a single tube can have similar hybridization properties. The annealing temperature and primer concentration can be calculated to some extent or may also be used empirically. As non-specific hybridization increases each time a primer pair is added, reaction conditions should be modified whenever each primer pair is added. In addition, artifacts may occur due to depletion of the primer pair or the like. The use of 5'-tagged oligonucleotides in PCR reaction has been reported. However, a key feature of this amplification method is that it comprises a step of annealing of each primer and isolating primer extension reactions, and thus is not suitable for the actual multiplex PCR concept. Thus, creating perfect conditions for multiplex PCR is a very difficult and costly process. Therefore, it is necessary to develop a multiplex PCR method capable of simultaneously amplifying several targets to the same extent under the same conditions regardless of various characteristics of different primers.

Under this technical background, the inventors of this application have made extensive efforts to solve the above-described problems and develop a method for detecting methylated target DNA, which has high detection limit and accuracy, and as a result, have found that when target DNA is enriched by asymmetric linear amplification using a universal primer-linked oligonucleotide and is detected using this enriched target DNA as a template and a universal primer is linked to a target-specific oligonucleotide, methylated DNA can be detected with desired high sensitivity and accuracy, even if only one primer is added for multiplex detection of the target DNA, unlike a conventional art, thereby completing the present disclosure.

DISCLOSURE OF INVENTION

Technical Problem

It is an object of the present disclosure to provide a method of detecting methylated DNA in a multiplex manner using a universal primer.

Another object of the present disclosure is to provide a composition for multiplex detection of methylated DNA, which comprises a universal primer.

Still another object of the present disclosure is to provide a kit for multiplex detection of methylated DNA, which comprises the composition.

Technical Solution

To achieve the above object, the present disclosure provides a method for detecting methylated DNA, comprising the steps of: method for detecting methylated DNA, comprising: (a) treating a target DNA-containing sample with at least one reagent which modifies a non-methylated DNA site to be distinguished from a methylated DNA site; (b) constructing an oligonucleotide, which comprises a target-specific sequence designed to be capable of binding complementarily to the target DNA treated with the reagent, and a universal primer that does not bind complementarily to the target DNA; (c) performing one direction asymmetric linear amplification using, as a template, the target DNA treated with the reagent in step (a), and using, as a primer, the oligonucleotide constructed in step (b); (d) amplifying the target DNA using an oligonucleotide, which is capable of binding complementarily to the DNA linearly amplified in step (c), and a universal primer; and (e) detecting methylation of the target DNA by a probe capable of hybridizing complementarily to the target DNA sequence amplified in step (d).

The present disclosure also provides a composition for detecting methylated DNA, comprising: at least one reagent treated to a target DNA-containing sample, which modify a non-methylated DNA to be distinguished from a methylated DNA; an oligonucleotide, which comprises a target-specific sequence capable of binding complementarily to a target DNA sequence treated with the reagent, and a universal primer that does not bind complementarily to the target DNA; an oligonucleotide, which are capable of binding complementarily to a linearly amplified target DNA, and a universal primer; and a probe capable of hybridizing complementarily to the linearly amplified target DNA sequence.

The present disclosure also provides a kit for detecting methylated DNA, which comprises the composition.

BRIEF DESCRIPTION OF THE DRAWINGS

FIG. 1 is a conceptual view schematically showing a method for multiplex detection of methylated target DNA.

FIG. 2 shows the results of comparing the sensitivity of detection of methylated DNA between a method of the present disclosure and a conventional method.

FIG. 3 schematically shows a process of designing primers and a probe for target DNA, which are used in a method of the present disclosure.

FIGS. 4a and 4b show the results of comparing the sensitivity of detection of methylated DNA between a method of the present disclosure, which is performed using primers and a probe for target DNA, and a conventional method.

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

In one aspect, the present disclosure is directed to a method for detecting methylated DNA, comprising the steps of: (a) treating a target DNA-containing sample with at least one reagent which modifies a non-methylated DNA site to be distinguished from a methylated DNA site;

(b) constructing an oligonucleotide, which comprises a target-specific sequence designed to be capable of binding complementarily to the target DNA treated with the reagent, and a universal primer that does not bind complementarily to the target DNA;

(c) performing one direction asymmetric linear amplification using, as a template, the target DNA treated with the reagent in step (a), and using, as a primer, the oligonucleotide constructed in step (b);

(d) amplifying the target DNA using an oligonucleotide, which is capable of binding complementarily to the DNA linearly amplified in step (c), and a universal primer that does not bind complementarily to the linearly amplified target DNA; and (e) detecting methylation of the target DNA by a probe capable of hybridizing complementarily to the target DNA sequence amplified in step (d).

In the present disclosure, a method capable of early diagnosing disease by detecting methylated DNA with high sensitivity was developed, and the performance of the method was examined. In one example of the present disclosure, an internal control gene and a target DNA were first linearly amplified using a target-specific sequence capable of binding complementarily to the target DNA, and a universal primer that does not bind complementarily to the target DNA bound to the target-specific sequence, and then methylated DNA was analyzed by a detection method using an oligonucleotide capable of binding complementarily to a sequence complementary to the target DNA, a probe capable of hybridizing complementarily to the target DNA sequence, and the universal primer that does not bind complementarily to the linearly amplified target DNA. As a result, it was confirmed that the method of the present disclosure could detect methylated DNA with higher sensitivity and accuracy than a conventional method.

Specifically, fecal DNA derived from normal person, and fecal DNA derived from patients with colorectal cancer at each stage, were treated with bisulfite, and non-methylated cytosines were all converted to uracil, and then the DNAs were linearly amplified using an oligonucleotide which is capable of binding specifically to each of methylated SDC2 (target DNA) and COL2A1 (internal control) and capable of binding complementarily to the target DNA fused with a universal primer, after which real-time PCR was performed using a specific probe capable of hybridizing to each target probe, an oligonucleotide capable of binding complementarily to a sequence complementary to the target DNA, and the universal primer (FIG. 1). As a result, it could be confirmed that the method of the present disclosure could detect methylated DNA with higher sensitivity and accuracy than a conventional qMSP (quantitative methylation specific PCR) performed using a primer that does not comprise the universal primer (FIGS. 2 and 4).

In the present disclosure, step (a) is a step of treating a target DNA-containing sample with at least one reagent which modifies a non-methylated DNA site to be distinguished from a methylated DNA site.

"Methylation" as used in the present disclosure means that a methyl group is attached to the $5^{th}$ carbon atom of the cytosine base ring to form 5-methylcytosine (5-mC). 5-methylcytosine (5-mC) is always attached only to the C of a CG dinucleotide (5'-mCG-3'), which is frequently marked CpG. The C of CpG is mostly methylated by attachment with a methyl group. The methylation of this CpG inhibits a repetitive sequence in genomes, such as Alu or transposon, from being expressed. In addition, this CpG is a site where an epigenetic change in mammalian cells appears most often. The 5-mC of this CpG is naturally deaminated to T, and thus, the CpG in mammal genomes shows only 1% of frequency, which is much lower than a normal frequency (¼×¼=6.25%).

Regions in which CpGs are exceptionally integrated are known as CpG islands. The term "CpG islands" refer to sites which are 0.2-3 kb in length, and have a C+G content of more than 50% and a CpG ratio of more than 3.75%. There are about 45,000 CpG islands in the human genome, and they are mostly found in promoter regions regulating the expression of genes. Actually, the CpG islands occur in the promoters of housekeeping genes accounting for about 50% of human genes.

The presence of CpG methylation in the target DNA may be an indicator of disease. For example, CpG methylation of any one of the promoter, 5'-untranslated region and intron of the target DNA may be measured.

A CpG-containing gene is generally DNA. However, the method of the present disclosure may be applied to a sample containing DNA or a sample containing DNA and RNA, including mRNA, wherein the DNA or RNA may be single-stranded or double-stranded. Alternatively, the sample may also be a sample containing a DNA-RNA hybrid.

A nucleic acid mixture may also be used. As used herein, the term "multiplex" includes both the case in which there are a plurality of specific nucleic sequence regions to be detected in one kind of gene and the case in which a single tube (single reactor) includes a plurality of target DNAs. The specific nucleic acid sequence to be detected may be a large molecular fraction, and the specific sequence may be present from the beginning in the form of an isolated molecule constituting the entire nucleic acid sequence. The nucleic acid sequence need not be a nucleic acid present in a pure form, and the nucleic acid may be a small fraction in a complex mixture such as one containing the whole human DNA.

Specifically, the present disclosure is directed to a method for detecting a plurality of target DNA methylations in samples in a single reactor, wherein the sample may contain a plurality of multiple target DNAs. The target DNA may be used without limitation as long as it is not only a control gene, but also any gene that affects the development or progression of cancer when it expression is inhibited by abnormal methylation.

The sample may be derived from the human body. For example, the sample may be derived from liver cancer, glioblastoma, ovarian cancer, colon cancer, head and neck cancer, bladder cancer, renal cell cancer, gastric cancer, breast cancer, metastatic cancer, prostate cancer, pancreatic cancer, or lung cancer patients. In the present disclosure, the sample may be any one selected from among solid or liquid tissue, cells, feces, urine, blood, serum and plasma.

At least one reagent that modifies a non-methylated DNA site to be distinguished from a methylated DNA site can be used without limitation as long as it can distinguish between a non-methylated cytosine base and a methylated cytosine base. For example, the reagent may be one or more selected from among bisulfite, hydrogen sulfite, disulfite, and combinations thereof, but is not limited thereto. Specifically, a cytosine base methylated by the reagent is not converted, but a cytosine base unmethylated by the reagent may be converted to uracil or to another base other than or cytosine.

In the present disclosure, step (b) is a step of constructing an oligonucleotide, which comprises a target-specific sequence designed to be capable of binding complementarily to the target DNA treated with the reagent, and a universal primer that does not bind complementarily to the target DNA.

For common multiplex PCR, pairs of forward and reverse primers, which correspond to the number of targets, should be constructed and used simultaneously. However, in the method of the present disclosure, only one target-specific sequence (reverse primer) capable of binding complementarily to a target DNA sequence by a universal primer may be used in a real-time PCR process for simultaneously detecting several multiple methylated DNAs, and only an oligonucleotide (forward primer) capable of binding complementarily to the linearly amplified DNA may be used in the same number as the targets to be detected. Accordingly, only a small number of primers may be used for simultaneous detection of methylation of several targets, and thus the complexity of PCR and variation of PCR efficiency are reduced.

The target-specific sequence is a sequence capable of binding complementarily to a target DNA, and as the target-specific sequence, a sequence capable of binding complementarily to a methylated site of the target DNA, as well as a sequence capable of binding complementarily to a non-methylated site of the target DNA may also be used selectively.

The target-specific sequence may comprise, for example, one or more CpG dinucleotides. Specifically, the target-specific sequence may comprise a sequence having an identity of at least 50%, specifically, at least 55%, 60%, 70%, 80% or 90%, to one or more sequences selected from the group consisting of sequences represented by SEQ ID NOs: 2, 5, 9, 14, 17, 21 and 26.

The universal primer that can be used in the present disclosure is may be linked to either any one of a target-specific sequence (reverse primer) capable of binding complementarily to a target DNA sequence and an oligonucleotide (forward primer) capable of binding complementarily to the linearly amplified DNA, or both the reverse primer and the forward primer.

The universal primer can be used without limitation as long as it comprises a nucleotide sequence that does not bind complementarily to a target DNA amplifiable irrespective of the target DNA, but for example, may comprise a nucleotide sequence that is not present in the human genome. Specifically, the universal primer may comprise a sequence having an identity of at least 50%, specifically, at least 55%, 60%, 70%, 80% or 90%, to a nucleotide sequence represented by SEQ ID NO: 7. In addition, the universal primer may comprise a sequence such as T7, SP6, M13 or the like, but is not limited thereto.

Further, the universal primer may be one or more sequences selected from the group consisting of sequences represented by SEQ ID NOs: 35 to 41. The universal primer may be, for example, a T7 sequence of 5'-TAATACGACT-CACTATAGG-3' (SEQ ID NO: 35), an SP6 sequence of 5'-TATTTAGGTGACACTATAG-3' (SEQ ID NO: 36), or an M13 sequence of 5'-GTAAAACGACGGCCAG-3 (SEQ ID NO: 37: -20F), 5'-GTTTTCCCAGTCACGAC-3'(SEQ ID NO: 38: -40F), 5'-CGCCAGGGTTTTCCCAGTCACGAC-3' (SEQ ID NO: 39: -47F), 5'-GAAACAGCTATGAC-CATG-3' (SEQ ID NO: 40: R) or 5'-AGCGGATAACAAT-TTCACACAGG-3' (SEQ ID NO: 41: -48R).

The method of the present disclosure comprises a step (c) of performing asymmetric linear amplification using, as a template, the target DNA treated with the reagent in step (a), and using, as a primer, the oligonucleotide constructed in step (b).

A DNA treated with bisulfite in a real-time PCR process through the step (c) was not used immediately, but a linearly amplified DNA was used, and thus a detection rate and the sensitivity of detection are excellent (FIGS. 2 and 4).

In the present disclosure, only a target DNA is asymmetrically amplified linearly in one direction, and thus this leads to enrichment of the target DNA. In one embodiment, linear amplification for enriching a methylated target DNA may be performed by unidirectional PCR using as a primer an oligonucleotide comprising a universal primer bound to the 5' end of a target-specific sequence.

The linear amplification means that an amplification product is produced linearly with respect to the number of amplification cycles, including double-strand denaturation, primer annealing and nucleic acid synthesis. The linear amplification is distinguished from a polymerase chain reaction (PCR) that produces an amplification product exponentially with respect to the number of amplification cycles.

Next, the method of the present disclosure comprises a step (d) of amplifying the target DNA using an oligonucleotide, which is capable of binding complementarily to the DNA linearly amplified in step (c), and the universal primer.

In some cases, step (d) may further comprise a step of detecting methylation of the target DNA by use of a self-reporting or energy transfer labeled primer.

As used herein, the term "self-reporting" is also named "energy transfer labeled", and may be used interchangeably with "energy transfer labeled". As used herein, "self-reporting universal primer" may be used interchangeably with the term "energy transfer labeled primer".

"Self-reporting" or "energy transfer labeled" means that the primer is capable of self-quenching or self-probing such that when amplification does not occur, fluorescence is not emitted due to self-quenching, but when amplification occurs, quenching is released and fluorescence is emitted. Self-reporting or energy transfer-labeled substances include, but are not limited to, TaqMan probes, fluorophores and molecular beacons.

In one example, the oligonucleotide (forward primer) capable of binding complementarily to the linearly amplified DNA may comprise a sequence capable of binding complementarily to the target DNA constructed in step (d) and amplifying the target DNA, for example, one or more CpG dinucleotides.

Specifically, the oligonucleotide may comprise a sequence having an identity of at least 50%, specifically, at least 55%, 60%, 70%, 80% or 90%, to one or more sequences selected from the group consisting of sequences represented by SEQ ID NOs: 1, 4, 8, 10 to 13, 15, 16, 18 to 20, 22 to 25, 27 and 28.

The description of the universal primer is applied in the same manner as in step (b) as mentioned above.

The method of the present disclosure comprises a step (e) of detecting methylation of the target DNA by a probe capable of hybridizing complementarily to the target DNA sequence amplified in step (d).

In one example, the detection of methylation may be performed by any one method selected from the group consisting of PCR, methylation specific PCR, real-time methylation specific PCR, PCR Using Methylated DNA-specific binding protein, PCR Using Methylated DNA-specific binding antibody, quantitative PCR, DNA chip Assay, sequencing, Sequencing-by-synthesis, and Sequencing-by-ligation.

Method for Detection of Methylation (1) Methylation-Specific PCR:

When genomic DNA is treated with bisulfite to detect methylation by the methylation-specific PCR, cytosine in the 5'-CpG'-3 region remains intact, if it was methylated, but the cytosine changes to uracil, if it was unmethylated. Accordingly, based on the base sequence converted after bisulfite treatment, PCR primer sets corresponding to a region having the 5'-CpG-3' base sequence are constructed. When genomic DNA is amplified by PCR, the PCR product is detected in the PCR mixture employing the primers corresponding to the methylated base sequence, if the genomic DNA was methylated, and this methylation can be quantitatively analyzed by agarose gel electrophoresis. Herein, the probe for detection of methylation may be a TaqMan probe, a molecular beacon probe, or a self-reporting or energy transfer-labeled probe, but is not limited thereto.

(2) Real-Time Methylation Specific PCR

Real-time methylation-specific PCR is a real-time measurement method modified from the methylation-specific PCR method and comprises treating genomic DNA with bisulfite, designing PCR primers corresponding to the methylated base sequence, and performing real-time PCR using the primers. Methods of detecting the methylation of the genomic DNA include two methods: a method of detection using a TanMan probe complementary to the amplified base sequence; and a method of detection using Sybergreen. Thus, the real-time methylation-specific PCR allows selective quantitative analysis of methylated DNA. Herein, a standard curve is plotted using an in vitro methylated DNA sample, and a gene containing no '-CpG-3' sequence in the base sequence is also amplified as a negative control group for standardization to quantitatively analyze the degree of methylation.

(3) PCR Using Methylated DNA-Specific Binding Protein, Quantitative PCR, and DNA Chip Assay When a protein binding specifically only to methylated DNA is mixed with DNA, the protein binds specifically only to the methylated DNA. Thus, either PCR using a methylation-specific binding protein or a DNA chip assay allows selective isolation of only methylated DNA.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA.

(4) Detection of Differential Methylation-Bisulfate Sequencing Method

Another method for detecting a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA.

(5) Bisulfite Sequencing Method

Another method for detecting a methylated CpG-containing nucleic acid comprises the steps of: contacting a nucleic acid-containing sample with an agent that modifies a non-methylated cytosine; and amplifying the CpG-containing nucleic acid in the sample by means of methylation-independent oligonucleotide primers. Herein, the oligonucleotide primers can amplify the nucleic acid without distinguishing modified methylated and non-methylated nucleic acids. The amplified product may be sequenced by the Sanger method using a sequencing primer or by a next-generation sequencing method linked with bisulfite sequencing for detection of methylated nucleic acid.

(6) Herein, the next-generation sequencing method may be performed by sequencing-by-synthesis and sequencing-by-ligation. This method is characterized in that a single DNA fragment is spatially separated in place of making a bacterial clone, and is amplified in situ (clonal amplification) and sequenced. Herein, it analyzes hundreds of thousands of fragments at the same time, and thus is called "massively parallel sequencing".

It is based on sequencing-by-synthesis, and relies on a method of obtaining a signal while sequentially attaching mono- or di-nucleotides. It includes pyrosequencing, ion torrent and Solexa methods.

NGS systems based on sequencing-by synthesis include a Roche 454 platform, an Illumina HiSeq platform, an Ion PGM platform (Life Technology), and a PacBio platform (Pacific BioSciences). The 454 and Ion PGM platforms use emersion PCR that is a clonal amplification method, and the HiSeq platform uses Bridge amplification. The sequencing-by-synthesis method analyzes a sequence by detecting phosphate which is generated when synthesizing a DNA while sequentially attaching single nucleotides, hydrogen ion, or a pre-labeled fluorescence dye. To detect a sequence, the 454 platform uses a pyrosequencing method employing phosphate, and the Ion PGM platform uses hydrogen ion detection. The HiSeq and PacBio platforms analyze a sequence by detecting fluorescence.

Sequencing-by-ligation is a sequencing technique employing DNA ligase, and is performed by identifying nucleotides at specific positions in a DNA nucleotide sequence. Unlike most sequencing techniques employing polymerase, sequencing-by-ligation does not use a polymerase, and uses the characteristic in that DNA ligase does not ligate a mismatch sequence. It includes a SOLiD system. In this technique, two bases are read in each step, and the reading steps are independently repeated five times through the primer reset process. Thus, each base is read twice to increase accuracy.

In the case of sequencing-by-ligation, among dinucleotide primer sets made of 16 combinations, dinucleotide primers corresponding to the nucleotide sequence of interest are sequentially ligated, and a combination of the ligations is analyzed, thereby determining the nucleotide sequence of the DNA of interest.

Regarding the primers that are used in the present disclosure, when the target DNA is treated with the reagent (e.g., bisulfite) in step (a), cytosine in the 5'-CpG'-3 region remains intact, if it was methylated, but the cytosine changes to uracil, if it was not methylated. Accordingly, based on the base sequence converted after reagent (e.g., bisulfite) treatment, PCR primers corresponding to a region having the 5'-CpG-3' base sequence may be constructed.

The primers may be designed to be "substantially" complementary to each strand of the locus to be amplified of a target DNA. This means that the primers must be sufficiently complementary to hybridize with their respective strands under polymerization reaction conditions.

Methylation of the product amplified by an oligonucleotide, which is capable of binding complementarily to the DNA linearly amplified, and the universal primer in step (d) is detected by a probe capable of hybridizing to the target DNA, and the probe can be used without limitation as long as it can hybridizing to the target DNA to detect the methylation, but may comprise, for example, one or more CpG dinucleotides. In addition, there is a method in which detection is performed using a self-reporting fluorescent substance or an energy transfer labeling primer, in addition to the above-described oligonucleotide or universal primer.

Specifically, the probe may comprise a sequence having an identity of at least 50%, specifically, at least 55%, 60%, 70%, 80% or 90%, to one or more sequences selected from the group consisting of sequences represented by SEQ ID NOs: 3, 6, 29, 30, and 31 to 34.

In some embodiments, the probe may have a reporter or a quencher attached to both ends. The reporter may be one or more selected from the group consisting of FAM (6-carboxyfluorescein), Texas red, HEX (2', 4', 5', 7'-tetrachloro-6-carboxy-4,7-dichlorofluorescein), JOE, Cy3, and Cy5. The quencher may be one or more selected from the group consisting of TAMRA (6-carboxytetramethyl-rhodamine), BHQ1, BHQ2 and Dabcyl. The quencher may be one or more selected from the group consisting of TAMRA (6-carboxytetramethyl-rhodamine), BHQ1, BHQ2 and Dabcyl.

In another aspect, the present disclosure is directed to a composition for detecting methylated DNA, comprising: at least one reagent treated to a target DNA-containing sample, which modify a non-methylated DNA to be distinguished from a methylated DNA;

an oligonucleotide, which comprises a target-specific sequence capable of binding complementarily to a target DNA sequence treated with the reagent, and a universal primer that does not bind complementarily to the target DNA;

an oligonucleotide, which are capable of binding complementarily to a linearly amplified target DNA, and a universal primer that does not bind complementarily to the linearly amplified target DNA; and a probe capable of hybridizing complementarily to the linearly amplified target DNA sequence.

The composition according to the present disclosure overlaps with the above-described constitutions, including performing treatment with at least one reagent which modifies methylated DNA and non-methylated DNA so as to be distinguished between each other, performing linear amplification using an oligonucleotide which amplifies target DNA treated with the reagent and comprises a target-specific sequence capable of binding complementarily to a target DNA sequence and a universal sequence that does not hybridize to the target DNA, and detecting methylated DNA using an oligonucleotide, which is capable of binding complementarily to the linearly amplified DNA, a universal primer and a probe, and thus the detailed description thereof is omitted.

In still another aspect, the present disclosure is directed to a kit for detecting methylation of a target DNA, which comprises the composition.

In one example, the kit may comprise a carrier means compartmentalized to receive a sample therein, a container that receives a reagent therein, a container containing PCR primers for amplification of a 5'-CpG-3' base sequence of a target DNA, and a container containing a probe for detecting an amplified PCR product.

Carrier means are suited for containing one or more containers such as vials, tubes, and the like, each of the containers comprising one of the separate elements to be used in the method. In view of the description provided herein of the inventive method, those of skill in the art can readily determine the apportionment of the necessary reagents among the containers.

EXAMPLES

Hereinafter, the present disclosure will be described in further detail with reference to examples. It will be obvious to a person having ordinary skill in the art that these examples are for illustrative purposes only and are not to be construed to limit the scope of the present disclosure.

Example 1

Determination of Detection Limit Using Methylated DNA Derived from Cell Line

HCT116, SW480 and HT-29 cell lines, which are human colorectal cancer cell lines, were purchased from the Korean Cell Line Bank (Seoul, Korea), and cultured in RPMI media (JBI, Seoul, South Korea) containing 10% fetal bovine serum (JBI, Seoul, South Korea), penicillin and streptomycin in an incubator at 37° C. under 5% carbon dioxide.

Genomic DNA was extracted using a QiaAmp DNA Mini kit (Qiagen, Hilden, Germany) and treated with sodium bisulfite by means of an EZ DNA Methylation-Gold kit (ZYMO Research, Irvine, USA). In brief, genomic DNA was treated with bisulfite at 65° C. for 2.5 hours, and then desulfonated by leaving it at room temperature for 20 minutes. Next, it was bound to a Zymo-Spin IC column (Zymo Research, Irvine, USA), and then extracted with 10 µl of distilled water and stored at 20° C.

In order to determine the detection limit of the method of the present disclosure compare it with a meSDC2-qMSP that does not comprise the LTE process, methylated DNA derived from the HCT116 cell line was dispensed at a concentration of 100 to 10 pg, and then mixed with 20 ng of a human leukocyte genomic DNA (BioChain Institiute Inc., Hayward, Calif.) amplified using an Illustra GenomiPhi V2 DNA Amplification Kit (GE Healthcare, Cleveland, USA), followed by serial dilution.

Next, the DNA was amplified linearly using an oligonucleotide, which comprises the universal primer of SEQ ID NO: 7 linked with the SDC2-specific sequence of SEQ ID NO: 2, and an oligonucleotide which comprises the universal primer of SEQ ID NO: 7 linked with the COL2A1-specific sequence of SEQ ID NO: 5, under the following conditions: 95° C. for 5 min, and then 35 cycles, each consisting of 95° C. for 15 sec and 60° C. for 1 min. Next, real-time PCR was performed using the probe of SEQ ID NO: 3, the oligonucleotide of SEQ ID NO: 1 that can bind complementarily to the linearly amplified DNA, the probe of SEQ ID NO: 6, the oligonucleotide of SEQ ID NO: 4 that can bind complementarily to the linearly amplified DNA, and the universal primer of SEQ ID NO: 7, under the following conditions: 95° C. for 5 min, and then 40 cycles, each consisting of 95° C. for 15 sec and 60° C. for 1 min. The experiment was repeated 24 times (Table 1 and FIG. 1). Then, the Ct (cycle threshold) value was analyzed using the Rotor Gene Q software.

TABLE 1

Primer and probe sequences

| SEQ ID NO: | Description | Sequences |
| --- | --- | --- |
| SEQ ID NO: 1 | Oligonucleotide capable of binding complementarily to SDC2 | 5'-GTAGAAATTAATAAGTGAGAGGGC-3' |
| SEQ ID NO: 2 | SDC2-specific sequence | 5'-*AAAGATTCGGCGACCACCGA* ACGACTCAAACTCGAAAACTCG-3' |
| SEQ ID NO: 3 | SDC2 probe | 5'-FAM-TTCGGGGCGTAGTTGCGGGCGG-3' |
| SEQ ID NO: 4 | Oligonucleotide capable of binding complementarily to COL2A1 | 5'-GTAATGTTAGGAGTATTTTGTGG*I*TA-3' |
| SEQ ID NO: 5 | COL2A1-specific sequence | 5'-*AAAGATTCGGCGACCACCGA* CTA*I*CCCAAAAAAAC CCAATCCTA-3' |
| SEQ ID NO: 6 | COL2A1 | probe 5'-Cy5-AGAAGAAGGGAGGGGTGTTAGGAGAGG-3' |
| SEQ ID NO: 7 | Universal primer | 5'-*AAAGATTCGGCGACCACCGA*-3' |

Underlined: CpG dinucleotide; italic: universal primer; I: inosine nucleotide
* the sequences of SEQ ID NO: 2 and SEQ ID NO: 5 are SDC2 and COL2A1 target specific sequences, respectively, and correspond to sequences other than the universal primer sequence of SEQ ID NO: 7, and an oligonucleotide comprising a target-specific sequence and a universal primer that does not hybridize to the target DNA was used as a primer.

As a result, it was confirmed that the conventional method showed a detection rate of 100% in 200 pg of DNA, but showed a detection rate of 37.5% in 20 pg and a detection rate of 0% in 10 pg, whereas the method of the present disclosure showed a detection of 100% in 200 pg to 20 pg and showed a detection rate of 33.3% even in 10 pg (FIG. 2 and Table 2).

TABLE 2

Comparison of detection rate between the conventional method (qMSP) and the method of the present disclosure (LTE-qMSP)

| DNA concentration (pg) | Number of detections of methylated DNA by LTE-qMSP | Detection rate | Number of detections of methylated DNA by qMSP | Detection rate |
|---|---|---|---|---|
| 10 | 8 out of 24 | 33.3 | 0 out of 24 | N.D |
| 20 | 24 out of 24 | 100 | 9 out of 24 | 37.5 |
| 50 | 24 out of 24 | 100 | 19 out of 24 | 79.2 |
| 100 | 24 out of 24 | 100 | 23 out of 24 | 95.8 |
| 200 | 24 out of 24 | 100 | 24 out of 24 | 100 |
| Negative control | 0 out of 24 | N.D | 0 out of 24 | N.D |

Example 2

Comparison Between LTE-qMSP and qMSP

In order to evaluate the ability of the SDC2 gene to diagnose colorectal cancer, 18 sets of methylation-specific detection primers and probes which can represent all CpG islands of the SDC2 gene were designed (Table 3), and LTE-qMSP was performed. To this end, genomic DNA was isolated (QIAamp DNA Stool Mini kit, Qiagen) from the feces of each of normal persons and 25 colorectal cancer patients, and treated with bisulfite by an EZ DNA methylation-Gold kit. Then, the DNA was extracted with 10 μl of sterile distilled water and used in LTE-qMSP (Linear Target Enrichment-Methylation-specific real time PCR). Using the bisulfite-treated genomic DNA as a template, linear target enrichment (LTE) was performed using the designed target-specific sequence (R) shown in Table 3 below (FIG. 3). The LTE reaction was performed using a Rotor-Gene Q PCR system (Qiagen) and a total of 20 μl of a PCR reaction solution (template DNA, 10 μl; 5× AptaTaq DNA Master (Roche Diagnostics), 4 μl; COL2A1 target-specific sequence, 1 μl (1 pmole); SDC2 target-specific sequence, 1 μl (1 pmole); D.W. 4 μl) under the following PCR conditions: treatment at 95° C. for 5 min, and then 35 cycles, each consisting of 95° C. for 15 sec and 60° C. for 1 min.

qMSP was performed using a Rotor-Gene Q PCR system (Qiagen). It was performed using a total of 40 μl of a PCR reaction solution (20 μl of a primary LTE product; 8 μl of 5× AptaTaq DNA Master (Roche Diagnostics); 1 μl (10 pmole) of a PCR primer capable of binding complementarily to DNA; 1 μl (10 pmole) of an oligonucleotide capable of binding complementarily to SDC2; DNA; 1 μl (5 pmole) of an oligonucleotide capable of binding complementarily to COL2A1; 1 μl (10 pmole) of a universal primer (SEQ ID NO: 7); 1 μl (5 pmole) of an SDC2 TaqMan probe; 1 μl (2.5 pmole) of a COL2A1 TaqMan probe; 6 μl of D.W.) under the following PCR conditions: treatment at 95° C. for 5 min, and then 40 cycles, each consisting of 95° C. for 15 sec and a suitable annealing temperature (58° C. to 61° C.) for 1 min. Whether the PCR product would be amplified was determined by measuring the cycle threshold (Ct) value. Methylated and non-methylated control DNAs were tested along with sample DNAs using an EpiTect PCR control DNA set (Qiagen, cat. no. 59695). As an internal control gene, the COL2A1 gene (Kristensen et al., 2008) was used.

TABLE 3

Primer and probe sequences for SDC2 gene LTE-qMSP

| Set | Primers | Sequences (5'→3') | Amplification product size (bp) | SEQ ID NO: |
|---|---|---|---|---|
| 1 | F1 | AAGAAAAGGATTGAGAAAAC | 155 | 8 |
|  | R1 | AAAGATTCGGCGACCACCGACGAAAAAAATTCCTACAAAATTACACG |  | 9 |
|  | Probe 1 | CGTGTAATTTTGTAGGAATTTTTTCG |  | 29 |
| 2 | F2 | GGTTTGTCGGTGAGTAGAGTCGGC | 124 | 10 |
|  | R1 | AAAGATTCGGCGACCACCGACGAAAAAAATTCCTACAAAATTACACG |  | 9 |
|  | Probe 1 | CGTGTAATTTTGTAGGAATTTTTTCG |  | 29 |
| 3 | F3 | GTTATAGCGCGGAGTCGCGGC | 97 | 11 |
|  | R1 | AAAGATTCGGCGACCACCGACGAAAAAAATTCCTACAAAATTACACG |  | 9 |
|  | Probe 1 | CGTGTAATTTTGTAGGAATTTTTTCG |  | 29 |
| 4 | F4 | GGTTTTCGGAGTTGTTAATC | 69 | 12 |
|  | R1 | AAAGATTCGGCGACCACCGACGAAAAAAATTCCTACAAAATTACACG |  | 9 |
|  | Probe 1 | CGTGTAATTTTGTAGGAATTTTTTCG |  | 29 |
| 5 | F5 | TTATTTGGGAGTTATATTGTC | 156 | 13 |
|  | R2 | AAAGATTCGGCGACCACCGACGCGCCGCGCCTCCCTCCCCG |  | 14 |
|  | Probe 2 | CGGGGAGGGAGGCGCGGCGCG |  | 30 |
| 6 | F6 | TTTTAGTCGTTTAGGGGAGTTC | 126 | 15 |
|  | R2 | AAAGATTCGGCGACCACCGACGCGCCGCGCCTCCCTCCCCG |  | 14 |
|  | Probe2 | CGGGGAGGGAGGCGCGGCGCG |  | 30 |
| 7 | F7 | CGTAGTCGCGGAGTTAGTGGTTTC | 152 | 16 |
|  | R3 | AAAGATTCGGCGACCACCGACGCTAACTTAAACTACG |  | 17 |
|  | Probe 3 | CGTAGTTTTTTTTAAGTTAGCG |  | 31 |
| 8 | F8 | CGCGTTGTTTTTAGATATTTC | 121 | 18 |
|  | R3 | AAAGATTCGGCGACCACCGACGCTAACTTAAACTACG |  | 17 |
|  | Probe 3 | CGTAGTTTTTTTTAAGTTAGCG |  | 31 |
| 9 | F9 | CGCGCGGATCGCGCGTTTTCGTC | 87 | 19 |
|  | R3 | AAAGATTCGGCGACCACCGACGCTAACTTAAACTACG |  | 17 |
|  | Probe 3 | CGTAGTTTTTTTTAAGTTAGCG |  | 31 |
| 10 | F10 | CGGTACGGGAAAGGAGTTCGCG | 113 | 20 |
|  | R4 | AAAGATTCGGCGACCACCGACGACACGAAATTAATACTCC |  | 21 |
|  | Probe 4 | CGGAGTATTAATTTCGTGTCG |  | 32 |
| 11 | F11 | GTAGAAATTAATAAGTGAGAGGGC | 144 | 1 |
|  | R5 | AAAGATTCGGCGACCACCGAACGACTCAAACTCGAAAACTCG |  | 2 |
|  | Probe5 | CGAGTTTTCGAGTTTGAGTCGT |  | 33 |
| 12 | F11 | GTAGAAATTAATAAGTGAGAGGGC | 144 | 1 |
|  | R5 | AAAGATTCGGCGACCACCGAACGACTCAAACTCGAAAACTCG |  | 2 |
|  | Probe 5-1 | TTCGGGGCGTAGTTGCGGCGG |  | 3 |
| 13 | F12 | TCGCGTTTTCGGGGCGTAGTTGC | 119 | 22 |
|  | R5 | AAAGATTCGGCGACCACCGAACGACTCAAACTCGAAAACTCG |  | 2 |
|  | Probe5 | CGAGTTTTCGAGTTTGAGTCGT |  | 33 |
| 14 | F13 | CGGCGGGAGTAGGCGTAGGAGGAGGAAGC | 93 | 23 |
|  | R5 | AAAGATTCGGCGACCACCGAACGACTCAAACTCGAAAACTCG |  | 2 |
|  | Probe 5 | CGAGTTTTCGAGTTTGAGTCGT |  | 33 |

TABLE 3-continued

Primer and probe sequences for SDC2 gene LTE-qMSP

| Set | Primers | Sequences (5'→3') | Amplification product size (bp) | SEQ ID NO: |
|---|---|---|---|---|
| 15 | F14 | AGGAAGCGAGCGTTTTCGAGTTTC | 71 | 24 |
| | R5 | *AAAGATTCGGCGACCACCGA*ACGACTCAAACTCGAAAACTCG | | 2 |
| | Probe 5 | CGAGTTTTCGAGTTTGAGTCGT | | 33 |
| 16 | F15 | AATCGTTGCGGTATTTTGTTTC | 133 | 25 |
| | R6 | *AAAGATTCGGCGACCACCGA*CCAAAAACCGACTACTCCCAACCG | | 26 |
| | Probe 6 | CGGTTGGGAGTAGTCGGTTTTTGG | | 34 |
| 17 | F16 | GATTCGTGTGCGCGGGTTGC | 110 | 27 |
| | R6 | *AAAGATTCGGCGACCACCGA*CCAAAAACCGACTACTCCCAACCG | | 26 |
| | Probe 6 | CGGTTGGGAGTAGTCGGTTTTTGG | | 34 |
| 18 | F17 | CGAGCGTTGGGTAGGAGGTTTC | 88 | 28 |
| | R6 | *AAAGATTCGGCGACCACCGA*CCAAAAACCGACTACTCCCAACCG | | 26 |
| | Probe 6 | CGGTTGGGAGTAGTCGGTTTTTGG | | 34 |

* Italic: universal sequence (SEQ ID NO: 7)
* Sequences of R1 to R6 are target-specific sequences which correspond to sequences other than the universal sequence of SEQ ID NO: 7.
* F1 to F17 correspond to oligonucleotides capable of binding complementarily to linearly amplified target DNA.

A. Results of Comparison Between LTE-qMSP and qMSP for Set 6

According to the method described in Example 1, the sensitivity of detection by set 6 was compared between the LTE-qMSP method and the qMSP method. As a result, it was confirmed that the conventional method showed a detection rate of 100% in 200 pg of DNA, but showed a detection rate of 37.5% in 20 pg and a detection rate of 0% in 10 pg, whereas the method of the present disclosure showed a detection rate of 100% in 200 pg to 20 pg and a detection rate of 33.3% even in 10 pg (FIG. 4a and Table 4).

TABLE 4

Comparison of detection rate between the conventional method (qMSP) and the method of the present disclosure (LTE-qMSP)

| DNA concentration (pg) | Number of detections of methylated DNA by LTE-qMSP | Detection rate | Number of detections of methylated DNA by qMSP | Detection rate |
|---|---|---|---|---|
| 10 | 8 out of 24 | 33.3 | 0 out of 24 | N.D |
| 20 | 24 out of 24 | 100 | 9 out of 24 | 37.5 |
| 50 | 24 out of 24 | 100 | 19 out of 24 | 79.2 |
| 100 | 24 out of 24 | 100 | 23 out of 24 | 95.8 |
| 200 | 24 out of 24 | 100 | 24 out o 24f | 100 |
| Negative control | 0 out of 24 | N.D | 0 out of 24 | N.D |

B. Results of Comparison Between LTE-qMSP and qMSP for Set 17

According to the method described in Example 1, the sensitivity of detection by set 17 was compared between the LTE-qMSP method and the qMSP method. As a result, it was confirmed that the qMSP method showed a detection rate of 100% in 200 pg of DNA, but showed a detection rate of 45.0% in 20 pg and a detection rate of 0% in 10 pg, whereas the method of the present disclosure showed a detection rate of 100% in 200 pg to 20 pg and a detection rate of 91.7% in 20 pg and a detection rate of 29.2% even in 10 pg (FIG. 4b and Table 5).

TABLE 5

Comparison of detection rate between the conventional method (qMSP) and the method of the present disclosure (LTE-qMSP)

| DNA concentration (pg) | Number of detections of methylated DNA by LTE-qMSP | Detection rate | Number of detections of methylated DNA by qMSP | Detection rate |
|---|---|---|---|---|
| 10 | 7 out of 24 | 29.2 | 0 out of 24 | N.D |
| 20 | 22 out of 24 | 91.7 | 11 out of 24 | 45.0 |
| 50 | 23 out of 24 | 95.8 | 18 out of 24 | 75.0 |
| 100 | 24 out of 24 | 100 | 23 out of 24 | 95.8 |
| 200 | 24 out of 24 | 100 | 24 out of 24 | 100 |
| Negative control | 0 out of 24 | N.D | 0 out of 24 | N.D |

Example 3

Evaluation of the Ability of SDC2 Gene to Diagnose Colorectal Cancer in Feces by LTE-qMSP The degree of methylation in each of the samples shown in Table 3 of Example 2 was measured by the Ct value, and the sensitivity and specificity of each primer and probe set were calculated by ROC curve analysis (MedCalc program, Belgium) (Table 6).

Methylation of the SDC2 gene was analyzed using fecal DNA derived from normal persons and colorectal cancer patients. As a result, it was confirmed that the sensitivity for diagnosis of colorectal cancer was as high as 76% (19/25) to 88.0% (22/25) and the specificity was as high as 88.0% (3/25) to 100% (0/25). This suggests that the use of methylation of the SDC2 gene is highly useful for diagnosis of colorectal cancer.

TABLE 6

Evaluation of the ability of SDC2 gene to diagnose colorectal cancer

| Primer and probe set | Cut-off (Ct) | P value | Sensitivity (%), n = 25 | Specificity (%), n = 25 |
|---|---|---|---|---|
| 1 | <32.1 | <0.001 | 76.0 | 92.0 |
| 2 | <32.0 | <0.001 | 80.0 | 96.0 |
| 3 | <32.3 | <0.001 | 76.0 | 88.0 |
| 4 | <32.1 | <0.001 | 80.0 | 92.0 |
| 5 | <32.0 | <0.001 | 84.0 | 96.0 |
| 6 | <32.5 | <0.001 | 88.0 | 92.0 |
| 7 | <32.5 | <0.001 | 76.0 | 96.0 |
| 8 | <32.2 | <0.001 | 80.0 | 88.0 |
| 9 | <32.3 | <0.001 | 88.0 | 100 |
| 10 | <32.5 | <0.001 | 76.0 | 92.0 |
| 11 | <32.0 | <0.001 | 80.0 | 100 |
| 12 | <32.0 | <0.001 | 88.0 | 92.0 |
| 13 | <32.1 | <0.001 | 88.0 | 88.0 |
| 14 | <32.0 | <0.001 | 84.0 | 92.0 |
| 15 | <32.2 | <0.001 | 80.0 | 96.0 |
| 16 | <32.3 | <0.001 | 76.0 | 100 |
| 17 | <32.5 | <0.001 | 84.0 | 100 |
| 18 | <32.0 | <0.001 | 88.0 | 96.0 |

In order to further evaluate the ability of the LTE-qMSP method for multiplex detection of methylation, the ability of a combination of set 1 and set 2 to diagnose colorectal cancer was evaluated using fecal DNA in a single tube.

TABLE 7

Evaluation of the ability of combination of set 1 and set 12 to diagnose colorectal cancer

| Primer and probe set | Cut-off (Ct) | P value | Sensitivity (%), n = 25 | Specificity (%), n = 25 |
|---|---|---|---|---|
| 1 + 12 | <32.2 | <0.001 | 88.0 | 92.0 |

Clinical verification of a combination of set 1 and set 12 was performed, and as a result, it was confirmed that the sensitivity and the specificity were as extremely high as 88% and 92%, respectively. Thus, it was confirmed again that it is possible to detect methylation using the LTE-qMSP method in which several methylated targets are simultaneously amplified in a single tube.

INDUSTRIAL APPLICABILITY

As described above, the method for detecting methylated DNA according to the present disclosure uses a universal primer, and hence can efficiently amplify multiple target DNAs even when using only one additional primer, even if a sample contains various kinds of genes. Furthermore, the complexity of PCR (real-time PCR) which is used to detect methylation by linear amplification can decrease, and variation in the efficiency of PCR can decrease, indicating that the sensitivity of detection is significantly high and the method is useful. In addition, the method has an advantage in that it can enrich methylated target DNA with higher specificity in the step of linearly amplifying the target DNA (LTE step).

Although the present disclosure has been described in detail with reference to the specific features, it will be apparent to those skilled in the art that this description is only for a preferred embodiment and does not limit the scope of the present disclosure. Thus, the substantial scope of the present disclosure will be defined by the appended claims and equivalents thereof.

The invention claimed is:

1. A method for detecting methylated DNA, comprising:
   (a) treating a target DNA-containing sample with bisulfite which modifies a non-methylated DNA site to be distinguished from a methylated DNA site;
   (b) constructing an oligonucleotide, which comprises a target-specific sequence designed to be capable of binding complementarily to the target DNA treated with the reagent, and a universal primer that does not bind complementarily to the target DNA;
   (c) performing one direction asymmetric linear amplification using, as a template, the target DNA treated with the reagent in step (a), and using, as a primer, the oligonucleotide constructed in step (b);
   (d) amplifying the target DNA using an oligonucleotide, which is capable of binding complementarily to the DNA linearly amplified in step (c), and a universal primer; and
   (e) detecting methylation of the target DNA by a probe capable of hybridizing complementarily to the target DNA sequence amplified in step (d).

2. The method of claim 1, wherein a plurality of target DNA methylations in samples in a single reactor is detected.

3. The method of claim 1, wherein the universal primer of the step (b) or (d) comprises a sequence having an identity of at least 50% to one or more sequences selected from the group consisting of nucleotide sequences represented by SEQ ID NOs: 7 and 35 to 41.

4. The method of claim 1, wherein the target-specific sequence of step (b) binds complementarily to a methylated site and/or a non-methylated site of the target DNA.

5. The method of claim 1, wherein the target-specific sequence of step (b) comprises one or more CpG dinucleotides.

6. The method of claim 1, wherein the target-specific sequence of step (b) comprises a sequence having an identity of at least 50% to one or more sequences selected from the group consisting of sequences represented by SEQ ID NOs: 2, 5, 9, 14, 17, 21 and 26.

7. The method of claim 1, wherein the detection of methylation is performed by any one method selected from the group consisting of PCR, methylation specific PCR, real-time methylation specific PCR, PCR Using Methylated DNA-specific binding protein, PCR Using Methylated DNA-specific binding antibody, quantitative PCR, DNA chip Assay, sequencing, Sequencing-by-synthesis, and Sequencing-by-ligation.

8. The method of claim 1, wherein the oligonucleotide of step (d) comprises one or more CpG dinucleotides.

9. The method of claim 1, wherein the oligonucleotide of step (d) comprises a sequence having an identity of at least 50% to one or more sequences selected from the group consisting of sequences represented by SEQ ID NOs: 1, 4, 8, 10 to 13, 15, 16, 18 to 20, 22 to 25, 27 and 28.

10. The method of claim 1, wherein the probe of step (e) comprises one or more CpG dinucleotides.

11. The method of claim 1, wherein the probe of step (e) comprises a sequence having an identity of at least 50% to one or more sequences selected from the group consisting of sequences represented by SEQ ID NOs: 3, 6, 29, 30, and 31 to 34.

12. A kit for detecting methylated DNA, comprising:
bisulfite, which modifies a non-methylated DNA to be distinguished from a methylated DNA of a target DNA-containing sample;
an oligonucleotide, which comprises a target-specific sequence capable of binding complementarily to a target DNA sequence treated with the reagent, and a universal primer that does not bind complementarily to the target DNA;
an oligonucleotide, which is capable of binding complementarily to a linearly amplified target DNA, and a universal primer; and
a probe capable of hybridizing complementarily to the linearly amplified target DNA sequence.

13. The kit of claim 12, constituted for detecting methylation of a plurality of target DNAs in a sample in a single reactor.

14. The kit of claim 12, wherein the universal primer comprises a sequence having an identity of at least 50% to one or more sequences selected from the group consisting of nucleotide sequences represented by SEQ ID NOs: 7 and 35 to 41.

15. The kit of claim 12, wherein the target-specific sequence binds complementarily to a methylated site and/or a non-methylated site of the target DNA.

16. The kit of claim 12, wherein the target-specific sequence comprises one or more CpG dinucleotides.

17. The kit of claim 12, wherein the target-specific sequence comprises a sequence having an identity of at least 50% to one or more sequences selected from the group consisting of sequences represented by SEQ ID NOs: 2, 5, 9, 14, 17, 21 and 26.

18. The kit of claim 12, wherein the oligonucleotide comprises one or more CpG dinucleotides.

19. The kit of claim 12, wherein the oligonucleotide comprises a sequence having an identity of at least 50% to one or more sequences selected from the group consisting of sequences represented by SEQ ID NOs: 1, 4, 8, 10 to 13, 15, 16, 18 to 20, 22 to 25, 27 and 28.

20. The kit of claim 12, wherein the probe comprises one or more CpG dinucleotides.

21. The kit of claim 12, wherein the probe comprises a sequence having an identity of at least 50% to one or more sequences selected from the group consisting of sequences represented by SEQ ID NOs: 3, 6, 29, 30, and 31 to 34.

22. A kit for detecting methylated DNA, which comprises:
at least one reagent for treating a target DNA-containing sample, to modify a non-methylated DNA to be distinguished from a methylated DNA, said at least one reagent comprising sodium bisulfite;
an oligonucleotide, which comprises a target-specific sequence capable of binding complementarily to a target DNA sequence treated with the reagent, and a universal primer that does not bind complementarily to the target DNA, said oligonucleotide comprising the universal primer of SEO ID NO: 7 linked with the SDC2-specific sequence of SEO ID NO: 2;
an oligonucleotide, which is capable of binding complementarily to a linearly amplified target DNA, and a universal primer, said oligonucleotide comprising the universal primer of SEQ ID NO: 7 linked with the COL2A1-specific sequence of SEQ ID NO: 5; and
a probe capable of hybridizing complementarily to the linearly amplified target DNA sequence, said probe comprising the COL2A1 probe of SEQ ID NO: 6.

* * * * *

UNITED STATES PATENT AND TRADEMARK OFFICE
CERTIFICATE OF CORRECTION

| | | |
|---|---|---|
| PATENT NO. | : 11,186,866 B2 | Page 1 of 1 |
| APPLICATION NO. | : 16/339694 | |
| DATED | : November 30, 2021 | |
| INVENTOR(S) | : Sung Whan An et al. | |

It is certified that error appears in the above-identified patent and that said Letters Patent is hereby corrected as shown below:

In the Claims

Column 32, Line 28, "SEO ID NO: 7" should be -- SEQ ID NO: 7 --.
Column 32, Line 29, "SEO ID NO: 2" should be -- SEQ ID NO: 2 --.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 41

<210> SEQ ID NO 1
<211> LENGTH: 24
<212> TYPE: DNA
<213> ORGANISM: Artificial Sequence
<220> FEATURE:
<223> OTHER INFORMATION: SDC2 complementrary oligo

<400> SEQUENCE: 1
gtagaaatta ataagtgaga gggc                                   24

<210> SEQ ID NO 2
<211> LENGTH: 42
<212> TYPE: DNA
<213> ORGANISM: Artificial Sequence
<220> FEATURE:
<223> OTHER INFORMATION: SDC2 specific seq

<400> SEQUENCE: 2
aaagattcgg cgaccaccga acgactcaaa ctcgaaaact cg               42

<210> SEQ ID NO 3
<211> LENGTH: 22
<212> TYPE: DNA
<213> ORGANISM: Artificial Sequence
<220> FEATURE:
<223> OTHER INFORMATION: SDC2 probe

<400> SEQUENCE: 3
ttcggggcgt agttgcgggc gg                                     22

<210> SEQ ID NO 4
<211> LENGTH: 25
<212> TYPE: DNA
<213> ORGANISM: Artificial Sequence
<220> FEATURE:
<223> OTHER INFORMATION: COL2A1 complementary oligo

<400> SEQUENCE: 4
gtaatgttag gagtattttg tggta                                  25

<210> SEQ ID NO 5

```
<211> LENGTH: 43
<212> TYPE: DNA
<213> ORGANISM: Artificial Sequence
<220> FEATURE:
<223> OTHER INFORMATION: COL2A1 specific seq

<400> SEQUENCE: 5
aaagattcgg cgaccaccga ctacccaaaa aaacccaatc cta          43

<210> SEQ ID NO 6
<211> LENGTH: 27
<212> TYPE: DNA
<213> ORGANISM: Artificial Sequence
<220> FEATURE:
<223> OTHER INFORMATION: COL2A1 probe

<400> SEQUENCE: 6
agaagaaggg aggggtgtta ggagagg                            27

<210> SEQ ID NO 7
<211> LENGTH: 20
<212> TYPE: DNA
<213> ORGANISM: Artificial Sequence
<220> FEATURE:
<223> OTHER INFORMATION: Universal primer

<400> SEQUENCE: 7
aaagattcgg cgaccaccga                                    20

<210> SEQ ID NO 8
<211> LENGTH: 20
<212> TYPE: DNA
<213> ORGANISM: Artificial Sequence
<220> FEATURE:
<223> OTHER INFORMATION: 1-F1

<400> SEQUENCE: 8
aagaaaagga ttgagaaaac                                    20

<210> SEQ ID NO 9
<211> LENGTH: 47
<212> TYPE: DNA
<213> ORGANISM: Artificial Sequence
<220> FEATURE:
<223> OTHER INFORMATION: 1-R1

<400> SEQUENCE: 9
aaagattcgg cgaccaccga cgaaaaaaat tcctacaaaa ttacacg      47

<210> SEQ ID NO 10
<211> LENGTH: 24
<212> TYPE: DNA
<213> ORGANISM: Artificial Sequence
<220> FEATURE:
<223> OTHER INFORMATION: 2-F2

<400> SEQUENCE: 10
ggtttgtcgg tgagtagagt cggc                               24

<210> SEQ ID NO 11
<211> LENGTH: 21
<212> TYPE: DNA
<213> ORGANISM: Artificial Sequence
<220> FEATURE:
<223> OTHER INFORMATION: 3-F3

<400> SEQUENCE: 11
```
gttatagcgc ggagtcgcgg c                                              21

<210> SEQ ID NO 12
<211> LENGTH: 20
<212> TYPE: DNA
<213> ORGANISM: Artificial Sequence
<220> FEATURE:
<223> OTHER INFORMATION: 4-F4

<400> SEQUENCE: 12
ggttttcgga gttgttaatc                                                20

<210> SEQ ID NO 13
<211> LENGTH: 21
<212> TYPE: DNA
<213> ORGANISM: Artificial Sequence
<220> FEATURE:
<223> OTHER INFORMATION: 5-F5

<400> SEQUENCE: 13
ttatttggga gttatattgt c                                              21

<210> SEQ ID NO 14
<211> LENGTH: 41
<212> TYPE: DNA
<213> ORGANISM: Artificial Sequence
<220> FEATURE:
<223> OTHER INFORMATION: 5-R2

<400> SEQUENCE: 14
aaagattcgg cgaccaccga cgcgccgcgc ctccctcccc g                        41

<210> SEQ ID NO 15
<211> LENGTH: 22
<212> TYPE: DNA
<213> ORGANISM: Artificial Sequence
<220> FEATURE:
<223> OTHER INFORMATION: 6-F6

<400> SEQUENCE: 15
ttttagtcgt ttaggggagt tc                                             22

<210> SEQ ID NO 16
<211> LENGTH: 24
<212> TYPE: DNA
<213> ORGANISM: Artificial Sequence
<220> FEATURE:
<223> OTHER INFORMATION: 7-F7

<400> SEQUENCE: 16
cgtagtcgcg gagttagtgg tttc                                           24

<210> SEQ ID NO 17
<211> LENGTH: 43
<212> TYPE: DNA
<213> ORGANISM: Artificial Sequence
<220> FEATURE:
<223> OTHER INFORMATION: 7-R3

<400> SEQUENCE: 17
aaagattcgg cgaccaccga cgctaactta aaaaaaaact acg                      43

<210> SEQ ID NO 18
<211> LENGTH: 23
<212> TYPE: DNA

```
<213> ORGANISM: Artificial Sequence
<220> FEATURE:
<223> OTHER INFORMATION: 8-F8

<400> SEQUENCE: 18
cgcgttgttt tttagatatt ttc                                          23

<210> SEQ ID NO 19
<211> LENGTH: 23
<212> TYPE: DNA
<213> ORGANISM: Artificial Sequence
<220> FEATURE:
<223> OTHER INFORMATION: 9-F9

<400> SEQUENCE: 19
cgcgcggatc gcgcgttttc gtc                                          23

<210> SEQ ID NO 20
<211> LENGTH: 22
<212> TYPE: DNA
<213> ORGANISM: Artificial Sequence
<220> FEATURE:
<223> OTHER INFORMATION: 10-F10

<400> SEQUENCE: 20
cggtacggga aggagttcg cg                                            22

<210> SEQ ID NO 21
<211> LENGTH: 41
<212> TYPE: DNA
<213> ORGANISM: Artificial Sequence
<220> FEATURE:
<223> OTHER INFORMATION: 10-R4

<400> SEQUENCE: 21
aaagattcgg cgaccaccga cgacacgaaa ttaatactcc g                      41

<210> SEQ ID NO 22
<211> LENGTH: 23
<212> TYPE: DNA
<213> ORGANISM: Artificial Sequence
<220> FEATURE:
<223> OTHER INFORMATION: 13-F 12

<400> SEQUENCE: 22
tcgcgttttc ggggcgtagt tgc                                          23

<210> SEQ ID NO 23
<211> LENGTH: 29
<212> TYPE: DNA
<213> ORGANISM: Artificial Sequence
<220> FEATURE:
<223> OTHER INFORMATION: 14-F13

<400> SEQUENCE: 23
cggcgggagt aggcgtagga ggaggaagc                                    29

<210> SEQ ID NO 24
<211> LENGTH: 24
<212> TYPE: DNA
<213> ORGANISM: Artificial Sequence
<220> FEATURE:
<223> OTHER INFORMATION: 15-F14

<400> SEQUENCE: 24
aggaagcgag cgttttcgag tttc                                         24
```

<210> SEQ ID NO 25
<211> LENGTH: 22
<212> TYPE: DNA
<213> ORGANISM: Artificial Sequence
<220> FEATURE:
<223> OTHER INFORMATION: 16-F15

<400> SEQUENCE: 25
aatcgttgcg gtattttgtt tc                                              22

<210> SEQ ID NO 26
<211> LENGTH: 44
<212> TYPE: DNA
<213> ORGANISM: Artificial Sequence
<220> FEATURE:
<223> OTHER INFORMATION: 16-R6

<400> SEQUENCE: 26
aaagattcgg cgaccaccga ccaaaaaccg actactccca accg                      44

<210> SEQ ID NO 27
<211> LENGTH: 20
<212> TYPE: DNA
<213> ORGANISM: Artificial Sequence
<220> FEATURE:
<223> OTHER INFORMATION: 17-F16

<400> SEQUENCE: 27
gattcgtgtg cgcgggttgc                                                 20

<210> SEQ ID NO 28
<211> LENGTH: 22
<212> TYPE: DNA
<213> ORGANISM: Artificial Sequence
<220> FEATURE:
<223> OTHER INFORMATION: 18-F17

<400> SEQUENCE: 28
cgagcgttgg gtaggaggtt tc                                              22

<210> SEQ ID NO 29
<211> LENGTH: 27
<212> TYPE: DNA
<213> ORGANISM: Artificial Sequence
<220> FEATURE:
<223> OTHER INFORMATION: Probe 1

<400> SEQUENCE: 29
cgtgtaattt tgtaggaatt tttttcg                                         27

<210> SEQ ID NO 30
<211> LENGTH: 21
<212> TYPE: DNA
<213> ORGANISM: Artificial Sequence
<220> FEATURE:
<223> OTHER INFORMATION: Probe 2

<400> SEQUENCE: 30
cggggaggga ggcgcggcgc g                                               21

<210> SEQ ID NO 31
<211> LENGTH: 23
<212> TYPE: DNA
<213> ORGANISM: Artificial Sequence
<220> FEATURE:

<223> OTHER INFORMATION: Probe 3

<400> SEQUENCE: 31
cgtagttttt ttttaagtta gcg                                           23

<210> SEQ ID NO 32
<211> LENGTH: 21
<212> TYPE: DNA
<213> ORGANISM: Artificial Sequence
<220> FEATURE:
<223> OTHER INFORMATION: Probe 4

<400> SEQUENCE: 32
cggagtatta atttcgtgtc g                                             21

<210> SEQ ID NO 33
<211> LENGTH: 22
<212> TYPE: DNA
<213> ORGANISM: Artificial Sequence
<220> FEATURE:
<223> OTHER INFORMATION: Probe 5

<400> SEQUENCE: 33
cgagttttcg agtttgagtc gt                                            22

<210> SEQ ID NO 34
<211> LENGTH: 24
<212> TYPE: DNA
<213> ORGANISM: Artificial Sequence
<220> FEATURE:
<223> OTHER INFORMATION: Probe 6

<400> SEQUENCE: 34
cggttgggag tagtcggttt ttgg                                          24

<210> SEQ ID NO 35
<211> LENGTH: 19
<212> TYPE: DNA
<213> ORGANISM: Artificial Sequence
<220> FEATURE:
<223> OTHER INFORMATION: T7 universal

<400> SEQUENCE: 35
taatacgact cactatagg                                                19

<210> SEQ ID NO 36
<211> LENGTH: 19
<212> TYPE: DNA
<213> ORGANISM: Artificial Sequence
<220> FEATURE:
<223> OTHER INFORMATION: SP6 universal

<400> SEQUENCE: 36
tatttaggtg acactatag                                                19

<210> SEQ ID NO 37
<211> LENGTH: 16
<212> TYPE: DNA
<213> ORGANISM: Artificial Sequence
<220> FEATURE:
<223> OTHER INFORMATION: M13 universal

<400> SEQUENCE: 37
gtaaaacgac ggccag                                                   16

```
<210> SEQ ID NO 38
<211> LENGTH: 17
<212> TYPE: DNA
<213> ORGANISM: Artificial Sequence
<220> FEATURE:
<223> OTHER INFORMATION: M13 universal

<400> SEQUENCE: 38
gttttcccag tcacgac                                                  17

<210> SEQ ID NO 39
<211> LENGTH: 24
<212> TYPE: DNA
<213> ORGANISM: Artificial Sequence
<220> FEATURE:
<223> OTHER INFORMATION: M13 universal

<400> SEQUENCE: 39
cgccagggtt ttcccagtca cgac                                          24

<210> SEQ ID NO 40
<211> LENGTH: 18
<212> TYPE: DNA
<213> ORGANISM: Artificial Sequence
<220> FEATURE:
<223> OTHER INFORMATION: M13 universal

<400> SEQUENCE: 40
gaaacagcta tgaccatg                                                 18

<210> SEQ ID NO 41
<211> LENGTH: 23
<212> TYPE: DNA
<213> ORGANISM: Artificial Sequence
<220> FEATURE:
<223> OTHER INFORMATION: M13 universal

<400> SEQUENCE: 41
agcggataac aatttcacac agg                                           23
```